(12) United States Patent
Chapelet et al.

(10) Patent No.: US 12,410,144 B2
(45) Date of Patent: Sep. 9, 2025

(54) TRIAZINANE DERIVATIVES AND METHODS OF MAKING THEM

(71) Applicant: FLEXSYS AMERICA L.P., St. Louis, MO (US)

(72) Inventors: Judicael Jacques Chapelet, Akron, OH (US); Leandro Forciniti, Allendale, NJ (US); Jonathan Michael Penney, Cuyahoga Falls, OH (US); Donald L. Fields, Jr., Copley, OH (US)

(73) Assignee: Flexsys America L.P., St. Louis, MO (US)

( * ) Notice: Subject to any disclaimer, the term of this patent is extended or adjusted under 35 U.S.C. 154(b) by 752 days.

(21) Appl. No.: 17/639,100

(22) PCT Filed: Aug. 26, 2020

(86) PCT No.: PCT/US2020/047861
§ 371 (c)(1),
(2) Date: Feb. 28, 2022

(87) PCT Pub. No.: WO2021/041452
PCT Pub. Date: Mar. 4, 2021

(65) Prior Publication Data
US 2022/0298123 A1    Sep. 22, 2022

Related U.S. Application Data (60) Provisional application No. 62/893,337, filed on Aug. 29, 2019.

(51) Int. Cl.
| | | |
|---|---|---|
| C07D 251/04 | (2006.01) |
| B60C 1/00 | (2006.01) |
| C08K 5/00 | (2006.01) |
| C08K 5/39 | (2006.01) |
| C10L 1/24 | (2006.01) |

(52) U.S. Cl.
CPC .......... *C07D 251/04* (2013.01); *B60C 1/0025* (2013.01); *C08K 5/005* (2013.01); *C08K 5/39* (2013.01); *C10L 1/2443* (2013.01)

(58) Field of Classification Search
CPC .................................................. C07D 251/04
See application file for complete search history.

(56) References Cited

U.S. PATENT DOCUMENTS

| | | |
|---|---|---|
| 3,732,192 A | 5/1973 | Arnold |
| 4,417,012 A | 11/1983 | Moniotte |
| 4,532,080 A | 7/1985 | Delseth et al. |
| 4,654,271 A | 3/1987 | Mauer et al. |
| 7,674,861 B1 | 3/2010 | York et al. |
| 11,905,256 B2 | 2/2024 | Chapelet et al. |
| 2015/0113858 A1 | 4/2015 | Brewer |
| 2023/0174495 A1 | 6/2023 | Chapelet et al. |

FOREIGN PATENT DOCUMENTS

| | | |
|---|---|---|
| CN | 110156719 A | 8/2019 |
| EP | 0070143 A1 | 1/1983 |
| EP | 0432417 A2 | 6/1991 |
| WO | WO-2010059363 A1 | 5/2010 |

OTHER PUBLICATIONS

International Search Report and Written Opinion for International Application No. PCT/US2019/057357, European Patent Office, Netherlands, mailed Jan. 20, 2020, 8 pages.

International Search Report and Written Opinion for International Application No. PCT/US2021/028064, European Patent Office, Netherlands, mailed on Jun. 9, 2021, 9 pages.

International Search Report and Written Opinion for International Application No. PCT/US2020/047861, European Patent Office, Netherlands, mailed on Nov. 20, 2020, 9 pages.

*Primary Examiner* — Paul V Ward
(74) *Attorney, Agent, or Firm* — Sterne, Kessler, Goldstein &Fox P.L.L.C.

(57) ABSTRACT

The present invention is directed to compounds represented by the formula I: wherein $R_1$ comprises a hydrogen atom or an alkyl group having 1 to 2 carbon atoms; wherein $R_2$ comprises an alkylene group, an arylene group, or a heterocyclic group; and wherein $R_3$, $R_4$, $R_5$, $R_6$, $R_7$, and $R_8$ are identical or different and comprise a hydrogen atom, an alkyl group, an aryl group, or an alkylaryl group.

20 Claims, 3 Drawing Sheets

Figure 1 (carbon 13 NMR spectrum):

Figure 2 (thermogravimetric chromatogram):

Figure 3 (differential scanning calorimetric chromatogram):

TRIAZINANE DERIVATIVES AND METHODS OF MAKING THEM

FIELD OF THE INVENTION

The present invention relates to triazinane derivatives and methods of making them. The triazinane compounds of the invention include three aminecarbotrithioate end-groups, making them particularly useful as rubber additives.

BACKGROUND OF THE INVENTION

Processes for vulcanizing diene rubbers by heating with sulfur and a vulcanization accelerator have been known for many years. By this process, vulcanized rubber compositions can be obtained that have such desirable properties as high tensile strength, resilience, and fatigue resistance. However, these compositions may lack desirable aging properties. Apart from the addition of antioxidants, which may retard oxidative heat aging, other methods which have been proposed include the use of lower proportions of sulfur and increased proportions of accelerator relative to those which would be employed for a conventional cure, and the partial or complete replacement of sulfur by other cross-linking agents.

Lowering the ratio of sulfur to accelerator, or replacing the sulfur partially or completely by an amine disulfide, can give vulcanizates having inferior dynamic properties. And the use of bis(sulfenamides) and compounds containing two or more accelerator groupings means that molecular species having accelerator activity as well as those having cross-linking activity are released into the vulcanizing system, so that the freedom for variations in compounding, which is possible when the cross-linking agent and the accelerator are added as separate entities, is lost.

However, the ionic character of a free thiosulfate moiety is not beneficial during rubber compounding. In some cases, it can even cause blooming in rubber post-mixing. This is believed to be due to poor compatibility of the ionic Bunte salt in the apolar rubber matrix. In addition, the expendable sulfite anion is cogenerated along with the desired hybrid crosslink upon vulcanization. In order to overcome these problems, non-ionic functions containing a disulfide bridge may be used. These neutral functions are superior to ionic thiosulfates in at least two respects: they are more compatible with the apolar rubber matrix; and they can be used to provide additional features such as cure acceleration by incorporating dithiocarbamate chemistry.

U.S. Pat. No. 4,417,012 discloses vulcanizable rubber compositions that comprise a diene rubber, sulfur, a vulcanization accelerator, and a stabilizer that contains two or more thiosulfate or thiosulfonate groups. The stabilizers disclosed provide vulcanized rubber compositions that demonstrate improved reversion and flex-life.

U.S. Pat. Appln. No. 62/753,949, filed Nov. 1, 2018 and incorporated herein by reference in its entirety, relates to triazinane compounds possessing three thiosulfate end-groups and methods of making them. These compounds are useful in the manufacture of vulcanized elastomeric articles.

There remains a need in the art for compounds that serve both as cross-linking agents and vulcanization accelerators.

SUMMARY OF THE INVENTION

In one aspect, the present invention is directed to compounds represented by the formula I:

wherein $R_1$ comprises a hydrogen atom or an alkyl group having 1 to 2 carbon atoms;

wherein $R_2$ comprises an alkylene group, an arylene group, or a heterocyclic group; and wherein $R_3$, $R_4$, $R_5$, $R_6$, $R_7$, and $R_8$ are identical or different groups and comprise a hydrogen atom, an alkyl group, or an aryl or alkaryl group.

In a second aspect, the present invention relates to methods of making the compounds of formula I, that comprise: reacting a compound of formula II:

wherein $R_1$ comprises a hydrogen atom or an alkyl group having 1 to 2 carbon atoms;

wherein $R_2$ comprises an alkylene group, an arylene group, or a heterocyclic group; and wherein M comprises a monovalent metallic cation such as sodium, lithium, or potassium; or a multivalent metallic cation such as zinc, nickel, iron, titanium, or cobalt; or an ammonium or alkyl ammonium cation derived by addition of proton(s) to a nitrogenous base, with a dithiocarbamate salt, to obtain the triazinane derivatives of the present invention.

In a further aspect, the present invention is directed to compositions that comprise the compounds of formula I, for example vulcanizable elastomeric formulations, as well as articles made from them.

Further aspects of the invention are as set out below and in the claims that follow. It should be understood that the description and specific examples are intended for purposes of illustration only and are not intended to limit the spirit and scope of the present invention.

DETAILED DESCRIPTION

As utilized herein, the following terms or phrases are defined as follows:

"Antidegradant" refers to a material that inhibits degradation (as caused by for example, through heat, light, oxidation, and/or ozonation), or manifestations thereof, of a composition, formulation or article to which it is added or applied.

"Antifatigue agent" refers to a material that improves the flex fatigue resistance of a composition, formulation or article to which it is added or applied after a period of in-service application time whereby the composition, formulation or article is subjected to thermal, oxidative, ozone and mechanical degradative forces.

"Antioxidant" refers to a material that inhibits oxidative degradation of a composition, formulation or article to which it is added or applied.

"Antiozonant" refers to a material that inhibits ozone exposure degradation of a composition, formulation or article to which it is added or applied.

"Elastomer" means any polymer which after vulcanization (or crosslinking) and at room temperature can be stretched under low stress, for example to at least twice its original length and, upon immediate release of the stress, will return with force to approximately its original length, including without limitation rubber.

"Vulcanizable Elastomeric Formulation" means a composition that includes an elastomer and that is capable of vulcanization when placed under vulcanization conditions.

The compounds of the invention are advantageously believed to increase the density of the cross-linked network of rubber compositions, as evidenced by improved reversion properties, and to accelerate the vulcanization.

In one aspect, the present invention is directed to compounds that are triazinane derivatives represented by formula I:

I wherein $R_1$ comprises a hydrogen atom or an alkyl group having 1 to 2 carbon atoms;
wherein $R_2$ comprises an alkylene group, an arylene group, or a heterocyclic group; and
wherein $R_3$, $R_4$, $R_5$, $R_6$, $R_7$, and $R_8$ are identical or different groups and comprise a hydrogen atom, an alkyl group, or an aryl or alkylaryl group.

According to one aspect of the invention, the triazinane derivatives of the invention may be prepared using triazinanes represented by formula II:

II wherein $R_1$ comprises a hydrogen atom or an alkyl group having from 1 to 2 carbon atoms;
wherein $R_2$ comprises an alkylene group having from 1 to 12 carbon atoms, an arylene group having from 5 to 18 carbon atoms, or a heterocyclic group having from 5 to 12 carbon atoms; and
wherein M comprises a monovalent metallic cation; a multivalent metallic cation; or an ammonium or alkyl ammonium cation derived by addition of one or more protons to a nitrogenous base.

These triazinane reactants include those disclosed and claimed in U.S. Pat. Appln. No. 62/753,949, filed Nov. 1, 2018 and incorporated herein by reference in its entirety. As well as being reactants according to the present invention, these compounds are themselves useful in the manufacture of vulcanized elastomeric articles. As these triazinane reactants have features in common with the triazinane derivatives of the present invention, including a triazinane core, the $R_1$ and $R_2$ groups, and a moiety possessing a sulfur-sulfur single-bond, those skilled in the art will readily comprehend that these features of the triazinane derivatives of the present invention are the same as, and may be derived from, the triazinanes of formula II which may be used as reactants.

Thus, the present invention relates to molecules bearing three aminecarbotrithioate end-groups, linked to a triazinane core via the $R_2$ group as described above. Without wishing to be bound by any theory, these molecules are believed to exhibit a dual effect: hybrid-crosslinking plus cure-acceleration. During processing of rubber, splitting of the disulfide bond is believed to generate two fragments: a tri-thiol radical, which reacts upon vulcanization with sulfur and up to three rubber chains to form flexible crosslinks (a "hybrid-crosslinking" effect); and a dithiocarbamate radical, which enables a "cure-acceleration" effect.

According to the invention, $R_1$ of formulas I and II may thus comprise a hydrogen atom or an alkyl group having 1 to 2 carbon atoms. Alkyl groups useful according to the invention thus include methyl and ethyl.

$R_2$ may comprise an alkylene group, an arylene group, or a heterocyclic group. Alkylene groups useful according to the invention include methylene, ethylene, propylene, and butylene, and more generally may be straight chain or branched alkyl groups having from 1-12 carbon atoms, or from 1-8 carbon atoms, or from 2-5 carbon atoms. Arylene groups useful according to the invention include phenylene, biphenylene, naphthalene, anthracene, indane, and fluorene, and may be substituted or unsubstituted. More generally, arylene groups include any arylene groups having from 5-18 carbon atoms, or from 6 to 12 carbon atoms, or from 6 to 8 carbon atoms, and may be substituted or unsubstituted. Heterocyclic groups that are useful according to the invention include both saturated and unsaturated heterocycles having from 5 to 12 carbon atoms, and aromatic heterocycles, and include indole, benzofuran, benzothiophene, carbazole, benzothiazole, and benzoxazole.

According to the invention, M may comprise monovalent metallic cation such as sodium, lithium, or potassium. Other monovalent metallic cations that are useful include silver, nickel, and thallium.

Alternatively, M may comprise a multivalent metallic cation such as zinc, nickel, iron, titanium, or cobalt. Other multivalent metallic cations useful according to the invention include platinum and palladium.

M may further comprise an ammonium or alkyl ammonium cation derived by addition of one or more protons to a nitrogenous base. These cations may be monovalent or multivalent cations, and include triethylammonium, tetrabutyl-ammonium, benzyltrimethylammonium, dimethyl-dioctadecylammonium, 2-hydroxyethan-1-ammonium, ethane-1,2-diammonium, benzene-1,4-diammonium, and diphenylethylenediammonium.

$R_3$, $R_4$, $R_5$, $R_6$, $R_7$, $R_8$ are identical or different groups and may comprise a hydrogen atom, an alkyl group, an aryl group, an alkylaryl group, or indeed any hydrocarbon moieties. Alkyl groups useful according to the invention include methyl, ethyl, propyl, and isopropyl and more generally may be straight chain or branched alkyl groups having from 1 to 18 carbon atoms, or 1 to 12 carbon atoms, or 1 to 6 carbon atoms. Aryl groups useful according to the invention include phenyl, biphenyl, naphthyl, anthracenyl, indanyl, and fluorenyl and more generally may be any aryl groups having from 6 to 18 carbon atoms. Other hydrocarbon moieties useful according to the invention include benzyl, allyl, and propargyl and more generally may be straight, branched, saturated, unsaturated, or any possible combinations, and more generally may be any hydrocarbon moieties having from 1 to 18 carbon atoms.

Compounds useful as reactants according to the invention thus include S,S',S"-((1,3,5-triazinane-1,3,5-triyl)tris(propane-3,1-diyl)) tris(sulfurothioate), S,S',S"-((1,3,5-triazinane-1,3,5-triyl)tris(ethane-2,1-diyl)) tris(sulfurothioate), S,S',S"-((1,3,5-triazinane-1,3,5-triyl)tris(methane-1,1-diyl)) tris(sulfurothioate), S,S',S"-((1,3,5-triazinane-1,3,5-triyl)tris(butane-4,1-diyl)) tris(sulfurothioate), and S,S',S"-((1,3,5-triazinane-1,3,5-triyl)tris(pentane-5,1-diyl))tris(sulfurothioate).

Compounds of the invention thus include (1,3,5-triazinane-1,3,5-triyl)tris(propane-3,1-diyl)tris(dibenzylcarbamo(dithioperoxo)thioate), (1,3,5-triazinane-1,3,5-triyl)tris(propane-3,1-diyl)tris(diethylcarbamo(dithioperoxo)thioate), (1,3,5-triazinane-1,3,5-triyl)tris(propane-3,1-diyl)tris(diphenylcarbamo(dithioperoxo)thioate), and (1,3,5-triazinane-1,3,5-triyl)tris(propane-3,1-diyl)tris(phenylcarbamo(dithioperoxo)thioate).

In another aspect, the invention relates to methods of making the compounds represented by formula I:

wherein $R_1$ comprises a hydrogen atom or an alkyl group having 1 to 2 carbon atoms;

wherein $R_2$ comprises an alkylene group, an arylene group, or a heterocyclic group; and wherein $R_3$, $R_4$, $R_5$, $R_6$, $R_7$, and $R_8$ are identical or different groups and comprise a hydrogen atom, an alkyl group, an aryl group, or an alkylaryl group.

According to this aspect, the compounds according to the invention may be produced by reacting a compound of formula II with a dithiocarbamate salt in aqueous media. Additives such as a formaldehyde source, an organic solvent, and a bicarbonate salt may be used but are not required.

The dithiocarbamate salts useful according to the invention may correspond, for example, to the compounds of formula III:

wherein R and R' are identical or different groups and may be $R_3$, $R_4$, $R_5$, $R_6$, $R_7$, and $R_8$ as already described with respect to formula I, for example a hydrogen atom or an alkyl, aryl, or alkylaryl group; and M' may be a monovalent metallic cation, a multivalent metallic cation, or an ammonium or alkyl ammonium cation derived by addition of one or more protons to a nitrogenous base. We have found sodium dibenzyldithiocarbamate to be a suitable dithiocarbamate salt. Other dithiocarbamate salts include, without limitation, dibenzylammonium dibenzyldithiocarbamate, potassium dibenzyldithiocarbamate, triethylammonium dibenzyldithiocarbamate, diethylammonium diethyldithiocarbamate, sodium diethyldithiocarbamate, potassium diethyldithiocarbamate, triethylammonium diethyldithiocarbamate, phenylammonium phenyldithiocarbamate, sodium phenyldithiocarbamate, potassium phenyldithiocarbamate, triethylammonium phenyldithiocarbamate, benzylmethylammonium benzylmethyldithiocarbamate, sodium benzylmethyldithiocarbamate, potassium benzylmethyldithiocarbamate, triethylammonium benzylmethyldithiocarbamate, and the like. Such dithiocarbamate salts useful according to the invention can be either synthesized or purchased when commercially available.

We have thus far demonstrated the invention with the use of aqueous formaldehyde. However, other suitable formaldehyde sources may be used, such as paraformaldehyde, 1,3,5-trioxane, pure formaldehyde gas, a solution of formaldehyde in solvent, or any combination of the aforementioned. Also, the invention could be illustrated without the use of formaldehyde.

We have thus far demonstrated the invention without the use of organic solvent. However organic solvents potentially suitable include, but are not limited to, toluene, benzene, hexanes, heptane, cyclohexane, chloroform, chlorobenzene, and ethyl acetate.

We have thus far demonstrated the invention without the use of bicarbonate salt. However, bicarbonate salts potentially suitable include, but are not limited to, sodium bicarbonate, potassium bicarbonate, lithium bicarbonate, ammonium bicarbonate, dimethylammonium bicarbonate, triethylammonium bicarbonate.

According to the invention, we thus propose the synthesis and characterization of an organic molecule possessing three aminecarbotrithioate end-groups and a triazinane core. The process may be carried out in water, and in certain aspects, the claimed compounds may easily be collected by ordinary vacuum filtration.

In another aspect briefly referenced above, the present invention is directed to a composition that includes at least one compound of the present invention as described above. The specific amount of the compound of the present invention that is included in the composition may vary widely depending on the intended application for the composition. It will be understood by one of ordinary skill in the art that the compositions of the present invention can include one or more compounds of the present invention such that the concentration of each individual compound necessary to achieve the desired efficacy is lower. Further, other known additives may be included in the composition such that a reduced amount of the compound of the present invention may be required to achieve the total desired efficacy.

In one embodiment that is exemplified in detail above, the composition of a present invention is a vulcanizable elastomeric formulation. The vulcanizable elastomeric formulation of the present invention includes at least one elastomer and the compounds of the present invention. Preferably, the compounds of the present invention are present in the vulcanizable elastomeric formulation in an amount of from 0.1 to 30 parts, preferably from 0.1 to 5.0 parts, per 100 parts elastomer.

The elastomer in the vulcanizable elastomeric formulation may be any vulcanizable unsaturated hydrocarbon elastomer known to one skilled in the art. These elastomers may include, without limitation, natural rubber or any synthetic rubber, for example diene-containing elastomers such as polymers formed from butadiene; isoprene; or combinations of styrene and butadiene, or styrene and isoprene, or styrene, butadiene and isoprene; or polymers formed from ethylene, propylene and diene monomers such as ethylidene norbornadiene or 1,5-hexadiene; or polymers formed from combinations of isobutylene, isoprene, and para-methyl-styrene. The latter potentially could be further halogenated with bromine or chlorine to further extend its usefulness in co-vulcanization with general purpose rubbers such as natural rubber and styrene-butadiene rubber. The vulcanizable elastomeric formulation may optionally also include other additives conventionally used in rubber processing, such as processing/flow aids, extenders, plasticizers, resins, adhesion promoters, antidegradants, coupling agents such as silanes or other promoters of filler-to-polymer interaction, bonding agents, buffers, fillers, pigments, activators, prevulcanization inhibitors, acid retarders, accelerators, fatty acids, zinc oxide, or other compounding ingredients or additives to further enhance the characteristics and/or improve the performance of the vulcanizable elastomeric formulation or the vulcanized elastomeric article from which it is formed Suitable accelerators may include, but not be limited to guanidines, thiazoles, sulfenamides, sulfenimides, dithiocarbamates, xanthates, thiurams, and combinations or mixtures thereof.

The vulcanizable elastomeric formulation of the present invention is useful in the manufacture of vulcanized elastomeric articles such as rubber belts and hoses, windshield wiper blades, vehicle tires and components thereof such as the tread, shoulder, sidewall and innerliner. Accordingly, in another aspect, the present invention is directed to a vulcanized elastomeric article with at least one component formed from the vulcanizable elastomeric formulation of the present invention. In one particular embodiment, the vulcanized elastomeric article is a vehicle tire, and the tire component is a sidewall. Alternatively, the vulcanized elastomeric article may be a reinforcing or structural tire component such as a belt ply compound or construction, a body ply compound or construction, a cover ply, a gum strip, or a composition such as a bead filler, an apex, a wedge, a chafer, a toe guard, a rim guard, or other high modulus component imparting durability to tire service, especially under repeated flexural stresses which may include high service loads.

While the foregoing aspects of the present invention have described utilities primarily focused on compositions related to vulcanized elastomeric article manufacture, it will be understood that the triazinanes of the present invention may also be useful in compositions for other utilities where aminecarbotrithioate functionality is desired. Accordingly, and as described above, the present invention in a general aspect is directed to a composition including the compounds of the present invention according to formula I and defined elsewhere herein. The compositions of the present invention therefore include the compounds of the present invention and optionally a carrier for the compound. Suitable carriers are substantially inert with respect to the compound and include waxes, oils, or solids such as carbon black or silica.

In a separate embodiment, the triazinanes of the present invention have a separate primary utility or functionality (such as a coating, lubricant, oil, fuel additive or fuel composition) and include a functional ingredient and the triazinanes of the present invention as a component. The functional ingredient is typically a degradable material such as a hydrocarbon but may also include other degradable materials. This embodiment therefore encompasses for example, a lubricant composition that includes a lubricant as the functional ingredient and the compound of the present invention. This embodiment further encompasses a combustible fuel composition that includes a combustible fuel as the functional ingredient and the compound of the present invention. This embodiment further encompasses a fuel additive composition that includes a fuel additive as the functional ingredient and the compound of the present invention.

A person skilled in the art will recognize that the measurements described herein are standard measurements that can be obtained by a variety of different test methods. The test methods described represents only one available method to obtain each of the required measurements.

The foregoing description of various embodiments of the invention has been presented for purposes of illustration and description. It is not intended to be exhaustive or to limit the invention to the precise embodiments disclosed. Numerous modifications or variations are possible, in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

Precursors for compounds of the present invention, the compounds of the present invention and methods for their manufacture are illustrated by the following examples, which are not intended in to any limit the spirit or scope of the present invention.

Analytical Methods

Moving die rheometers (Monsanto MDR 2000E) were used to determine cure characteristics of the rubber formulations. The instruments conform to ASTM standard D5289-17 and are defined as rotorless cure meters. A rubber test piece is contained in a die cavity which may be closed or almost closed and maintained at an elevated temperature. The cavity is formed by two dies one of which is oscillated through a small rotary amplitude. This action produces a sinusoidal shear torque which depends on the stiffness of the rubber compound. The stiffness of the rubber test piece increases as vulcanization proceeds. The test is completed when the recorded torque rises to either an equilibrium or maximum value or when a predetermined time has elapsed. A curve representing the torque at peak strain in one direction of the oscillation cycle is continuously recorded as a function of time. Critical parameters to report include MH which is the highest value measured by a torque transducer at the peak strain amplitude of the oscillating cycle (S') during a specified period of time when no plateau or maximum torque is obtained. ML which is the minimum S' torque in dN*m. T25 is equal to the time to satisfy this equation (ML+25*(MH−ML)/100). T90 is equal to the time to satisfy this equation (ML+90*(MH−ML)/100). The scorch time is defined as ts1 which is in minutes time to an increase of 1 unit of S' torque from ML value with an oscillation amplitude of +/−0.5.

Reversion, in percentage points, is calculated from measured torque values using a moving die rheometer per ASTM D5289 according to the following:

$$\text{Reversion \%} = [(M_H - M_F)/M_F] * 100$$

wherein a decrease in reversion is indicated by a decrease in the reversion percentage versus a control and wherein Torquemax ($M_H$) was defined above and $M_F$ is defined as the torque at the final time point obtained which for the examples below were 90 minutes.

Mooney viscometer with large rotor was used to determine the viscosity and pre-vulcanization characteristics of the rubber formulation containing the stabilized thiosulfates. Monsanto's Mooney MV 2000E conforming to ASTM D1646-17 was used. Part C test method where the viscosity of vulcanizable rubber compounds is recorded during heating at a specified temperature (i.e., 121 C) was run. The minimum viscosity and times for the viscosity increase by specified amounts are used as arbitrary measures of the start and rate of vulcanization. The difference between this method and the aforementioned method above is that this method cannot be used to study complete vulcanization because the continuous rotation of the disk will result in slippage when the specimen reaches a stiff consistency. However, given the historical significance of using this test to measure the incipient cure (scorch) time it is important to evaluate the improvement in scorch safety using this method in combination with the rotor less cure meters. The test specimens consisted of two test pieces of the rubber formulation having a combined volume of 25+/−3 cm³. A barrier film consistent with ASTM standard D1646 is used. The properly calibrated instrument is adjusted to a temperature of 121 C. The torque indicator is adjusted to zero read while the viscometer is running unloaded with the rotor in place. The disk is then stopped. After the hot rotor is removed one of the test pieces is punctured then the rotor is but back in place and the second test piece is placed on the center of the rotor. The dies are closed immediately and the timer turned on. A 1 minute lag between when the dies are closed is allowed to elapse, then the rotors are turned on. The viscosity is recorded and the following information is gathered: (1) Minimum viscosity. (2) The time 5 units of viscosity increase occurs ($t_5$). (3) The time 35 units in viscosity increase occurs ($t_{35}$). Here $t_5$ is defined as the time to scorch whereas $t_{35}$ is defined as the time to cure.

The indicator for rolling resistance (RR) is cured tangent delta at 100° C. (strain=10%; 10 Hz). This refers to the measure of energy loss at maximum torque in a rheometer and reflects the expected performance of rubber in terms of energy dissipation. Relatively lower numbers represent compounds with low energy losses thereby imparting lower (better) rolling resistance which is desirable in a tire for efficient fuel consumption. Accordingly, a decrease in rolling resistance is indicated by a decrease in cured tangent delta at 100° C. (strain=10%) versus a control.

The indicator for heat build-up rate (HB) is the temperature increasement rate measured according to ASTM D623 at 100° C. run for a duration of 30 minutes on Doli flexometer with numeric values in units of ° C./min. A decrease in heat build-up rate is indicated by a decrease in the numeric value of the temperature decreasement rate versus a control.

Example 1: Preparation of (1,3,5-triazinane-1,3,5-triyl)tris(propane-3,1-diyl)tris(dibenzylcarbamo(dithioperoxo)thioate)

To a 250 mL round bottom flask fitted with a stir-bar were charged the substrate sodium S,S',S''-((1,3,5-triazinane-1,3,5-triyl)tris(propane-3,1-diyl))tris(sulfurothioate) (8.30 g containing 10 wt % water; 12.13 mmol substrate), DI water (83 mL), and aqueous 37% formaldehyde (2.7 mL; 36.26 mmol formaldehyde). The slurry was stirred under $N_2$ protection for 5-10 min, then a freshly prepared solution of sodium dibenzyldithiocarbamate (36.405 mmol dithiocarbamate in 37 mL DI water) was added over 1-2 min. No exothermic event ensued. The reaction mixture was stirred at room temperature for 21-22 hours whereupon a light yellow solid separated. The latter was collected by vacuum filtration (Buchner—filter paper), triturated/washed with DI water (3×100 mL), and dried under vacuum at 40 deg C. for 1.5-2.0 hours. The product completely melted during drying step then solidified upon cooling to room temperature. The obtained mass was easily broken apart into a thin powder. Yield=8.52 g (62.5% of the theoretical) as a light-yellow powder.

Figure 1:
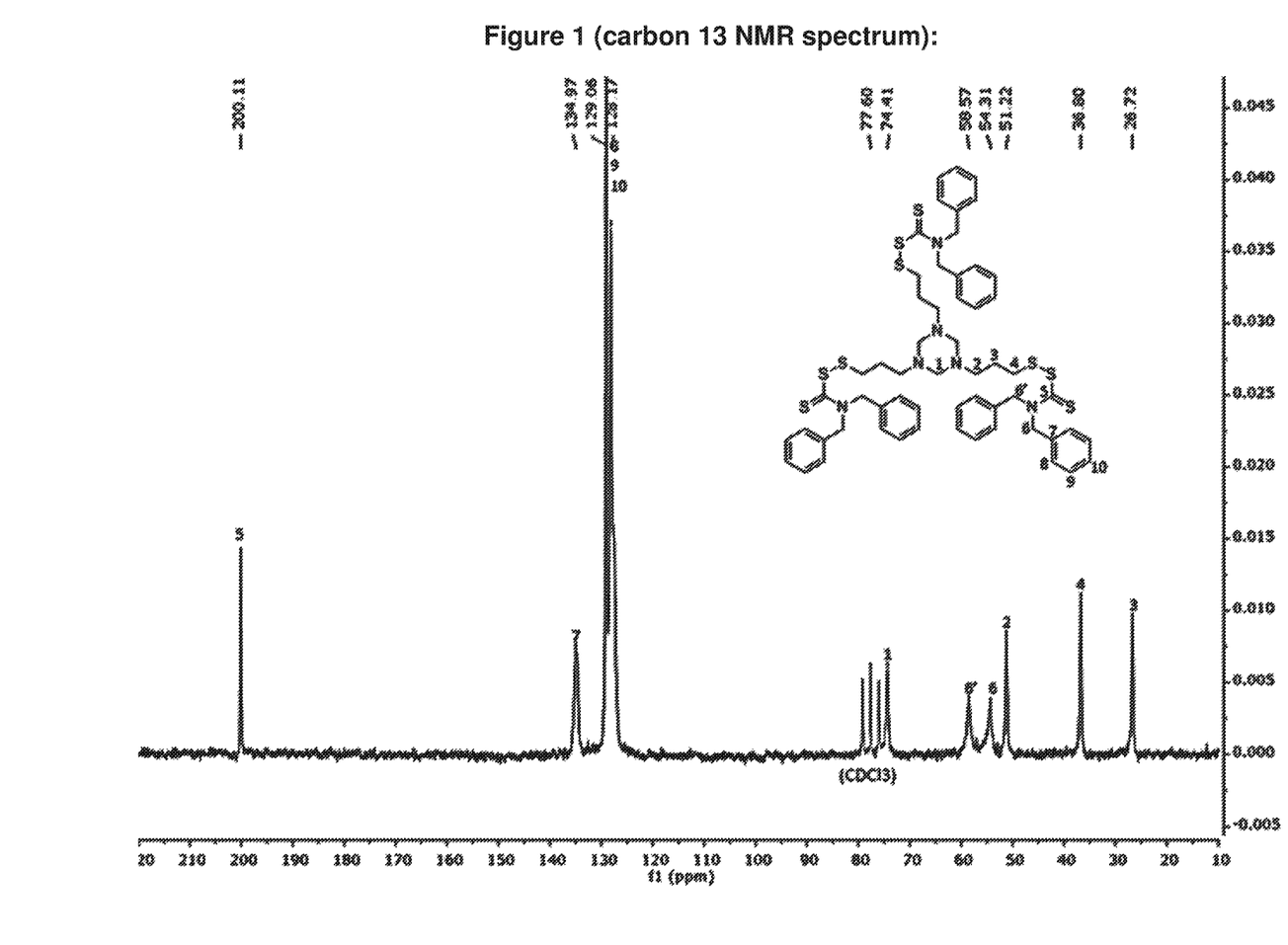
FIG. 1 depicts a carbon 13 NMR spectrum of (1,3,5-triazinane-1,3,5-triyl)tris(propane-3,1-diyl)tris(dibenzylcarbamo(dithioperoxo)thioate).
Figure 2:
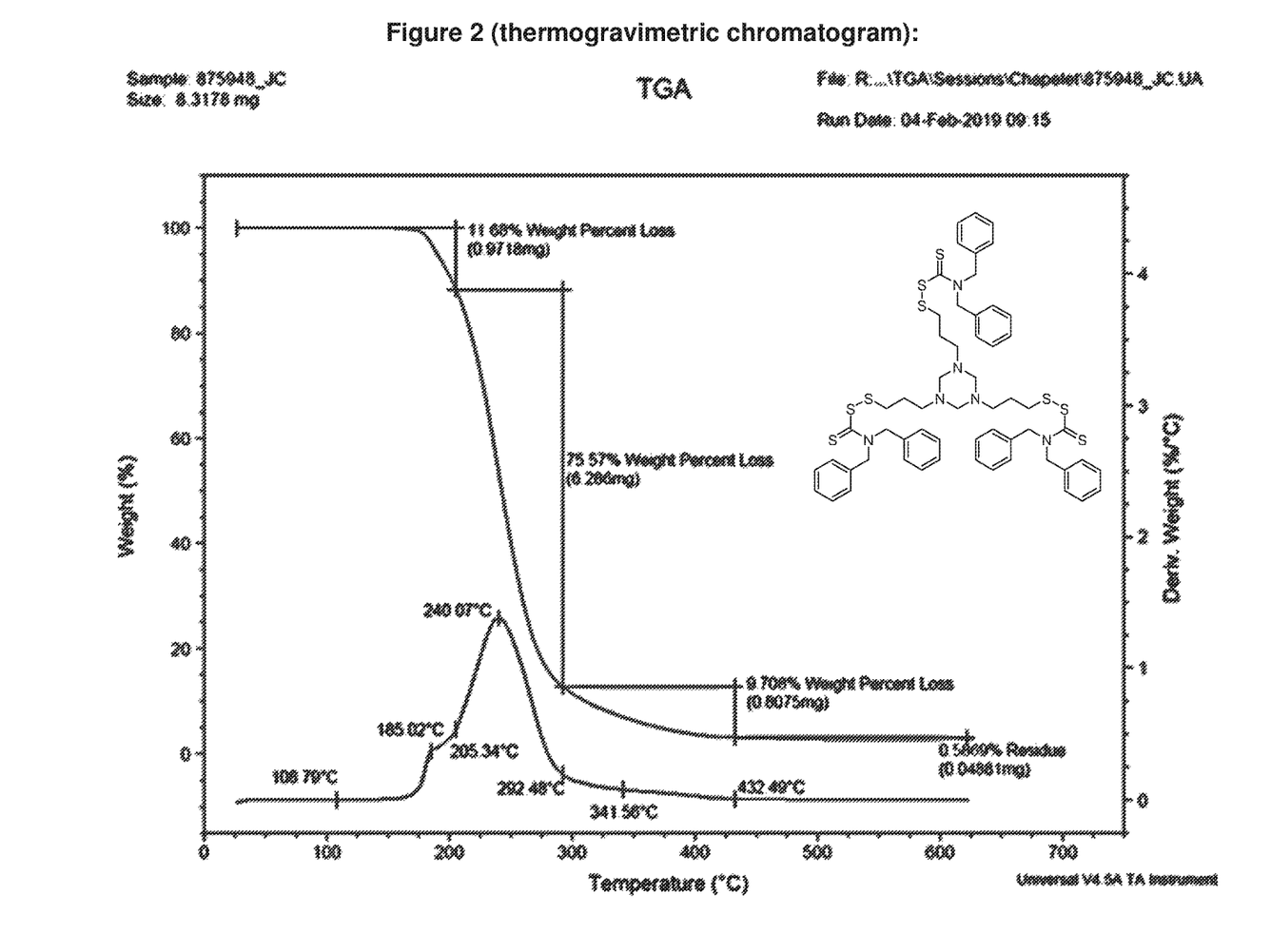
FIG. 2 depicts a thermogravimetric chromatogram of (1,3,5-triazinane-1,3,5-triyl)tris(propane-3,1-diyl)tris (dibenzylcarbamo(dithioperoxo)thioate).
Figure 3:
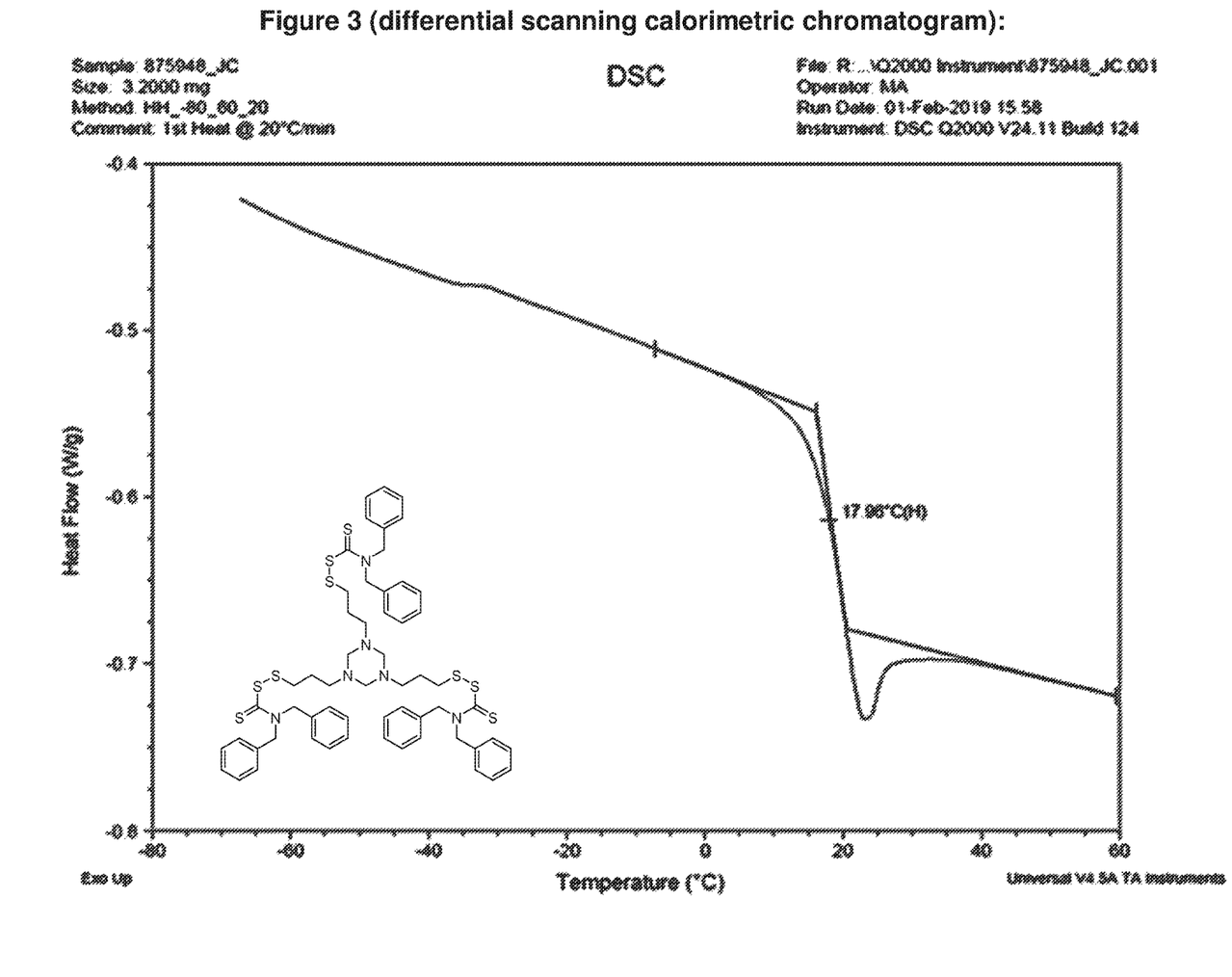
FIG. 3 depicts a differential scanning calorimetric chromatogram of (1,3,5-triazinane-1,3,5-triyl)tris(propane-3,1-diyl)tris(dibenzylcarbamo(dithioperoxo)thioate).

The solution of sodium dibenzyldithiocarbamate is typically prepared 30-60 min ahead of time: An equimolar mixture of dibenzylamine and sodium hydroxide in DI water (1 mol/L) is treated under stirring with an equimolar amount of carbon disulfide. The obtained light-yellow solution is involved in the above procedure without further purification. The nucleophilic thiolate moiety in sodium dibenzyldithiocarbamate cleanly attacks the thiosulfate at the $sp^3$ sulfur atom to form the disulfide bridge. One equivalent of sulfite anion is by-produced during this step. It is preferable to trap the reductant sulfite with formaldehyde to avoid cleavage of the disulfide bridge in the titled compound. Hence, the use of a stoichiometric amount of formaldehyde improves the chemoselectivity of such reaction. Analytical data of the final material are shown below in the figures.

An example was repeated as above using commercially available sodium diethyldithiocarbamate trihydrate as the dithiocarbamate salt. The following compound of formula I was obtained, along with some unknown impurities:

Example 2: Use of (1,3,5-triazinane-1,3,5-triyl)tris(propane-3,1-diyl)tris(dibenzylcarbamo(dithioperoxo)thioate) in Rubber Formulation This example illustrates the use of (1,3,5-triazinane-1,3,5-triyl)tris(propane-3,1-diyl)tris(dibenzylcarbamo(dithioperoxo)thioate) according to this invention in natural rubber formulation. A masterbatch having a composition presented in table 1 was used.

TABLE 1

| Material | Loading (phr) |
|---|---|
| Natural Rubber TSR 10 | 100 |
| N339 Carbon Black | 50 |
| Stearic Acid | 2 |
| Zinc Oxide | 8 |
| 6PPD | 2 |

A portion of the masterbatch was taken and mixed with Crystex HD OT 20, and N-tert-butyl-2-benzothiazole sulfenamide (Control 1). A further portion of the masterbatch was taken and mixed with Crystex HD OT 20, N-tert-butyl-2-benzothiazole sulfenamide, and (1,3,5-triazinane-1,3,5-triyl)tris(propane-3,1-diyl)tris(dibenzylcarbamo(dithioperoxo)thioate) (Example 1). The composition of both formulations (Control 1 and Example 1) is presented in table 2.

TABLE 2

| Material | Control 1 (phr) | Example 1 (phr) |
|---|---|---|
| Masterbatch | 162 | 162 |
| Crystex HD OT 20 (80% insoluble sulfur; 20% oil) | 5 | 5 |
| N-tert-butyl-2-benzothiazole sulfenamide | 0.9 | 0.9 |
| (1,3,5-triazinane-1,3,5-triyl)tris(propane-3,1-diyl)tris(dibenzylcarbamo(dithioperoxo)thioate) | 0 | 1 |

The results are summarized in table 3. Reversion resistance is defined as the difference in maximum torque and torque measured at 90 minutes normalized by the cure of the state which is the difference in maximum and minimum torque in the MDR measurement. The lower value of the reversion resistance indicates the rubber has better rubber network retention and is the desired direction. The curing kinetic performance can be assessed by the maximum curing rate and cure rate index (CRI). The maximum curing rate is the highest slope in the plot of measured torque versus time. It measures the maximum curing rate of the vulcanization process. The higher maximum curing rate indicates faster vulcanization kinetic and is the desired direction. The CRI is the measure of rate of vulcanization based on the difference between optimum vulcanization and the scorch time. The CRI is defined by the ASTM D 2084 as follow:

$$CRI=100/(T90-Ts1)$$

The higher CRI indicates the compound is faster curing and is the desired direction.

TABLE 3

| Test parameter | Control 1 | Example 1 |
|---|---|---|
| Reversion resistance at 150 deg C. (%) | 32 | 22 |
| Reversion resistance at 170 deg C. (%) | 51 | 36 |
| Maximum curing rate at 150 deg C. (dNm/min) | 5.96 | 38.84 |
| CRI at 150 deg C. (min$^{-1}$) | 14 | 84 |
| Maximum curing rate at 170 deg C. (dNm/min) | 16.33 | 88.69 |
| CRI at 170 deg C. (min$^{-1}$) | 47 | 244 |

It can be seen by the results presented in table 3 that improvement in both reversion resistance and accelerator properties (curing kinetic performance) can be achieved utilizing the molecule of the present invention.

The invention claimed is:

1. A compound represented by formula I:

I wherein $R_1$ is selected from the group consisting of a hydrogen atom and an alkyl group having 1 to 2 carbon atoms;

wherein $R_2$ is selected from the group consisting of an alkylene group having from 1 to 12 carbon atoms, an arylene group having from 5 to 18 carbon atoms, and a heterocyclic group having from 5 to 12 carbon atoms; and wherein $R_3$, $R_4$, $R_5$, $R_6$, $R_7$, and $R_8$ are independently selected from the group consisting of a hydrogen atom, an alkyl group, an aryl group, and an alkylaryl group.

2. The compound of claim 1, wherein $R_1$ is a hydrogen atom; wherein $R_2$ is an alkylene group having from 1 to 5 carbon atoms; and wherein $R_3$, $R_4$, $R_5$, $R_6$, $R_7$, and $R_8$ are independently selected from the group consisting of a hydrogen atom, an alkyl group having from 1 to 12 carbon atoms, an aryl group having from 1 to 12 carbon atoms, and an alkylaryl group having from 1 to 12 carbon atoms.

3. The compound of claim 1, wherein $R_1$ is a hydrogen atom; wherein $R_2$ comprises is an alkylene group having from 2 to 4 carbon atoms; and wherein $R_3$, $R_4$, $R_5$, $R_6$, $R_7$, and $R_8$ are independently selected from the group consisting of a hydrogen atom, an alkyl group having from 1 to 8 carbons, an aryl group having from 1 to 8 carbons, and an alkylaryl group having from 1 to 8 carbon atoms.

4. A compound selected from the group consisting of (1,3,5-triazinane-1,3,5-triyl)tris(propane-3,1-diyl)tris(dibenzylcarbamo-(dithioperoxo)thioate), (1,3,5-triazinane-1,3,5-triyl)tris(propane-3,1-diyl)tris(diethylcarbamo-(dithioperoxo)thioate), (1,3,5-triazinane-1,3,5-triyl)tris(propane-3,1-diyl)tris(phenylcarbamo-(dithioperoxo)thioate), and (1,3,5-triazinane-1,3,5-triyl)tris(propane-3,1-diyl)tris(benzylmethyl-carbamo(dithioperoxo)thioate).

5. The compound of claim 4, wherein the compound is (1,3,5-triazinane-1,3,5-triyl)tris(propane-3,1-diyl)tris(dibenzylcarbamo-(dithioperoxo)thioate).

6. The compound of claim 4, wherein the compound is (1,3,5-triazinane-1,3,5-triyl)tris(propane-3,1-diyl)tris(diethylcarbamo-(dithioperoxo)thioate).

7. The compound of claim 4, wherein the compound is (1,3,5-triazinane-1,3,5-triyl)tris(propane-3,1-diyl)tris(phenylcarbamo-(dithioperoxo)thioate).

8. The compound of claim 4, wherein the compound is (1,3,5-triazinane-1,3,5-triyl)tris(propane-3,1-diyl)tris(benzylmethyl-carbamo(dithioperoxo)thioate).

9. A stabilizer composition comprising the compound of claim 1 and a carrier for said compound.

10. A vulcanizable elastomeric formulation comprising an elastomer and the compound of claim 1.

11. The formulation of claim 10 wherein the compound is present in an amount of from 0.01 to 30 parts per 100 parts of elastomer.

12. The formulation of claim 10 wherein the compound is present in an amount of from 0.1 to 5.0 parts per 100 parts of elastomer.

13. A vulcanized elastomeric article formed from the vulcanizable elastomeric formulation of claim 10.

14. The vulcanized elastomeric article of claim 13 wherein said vulcanized elastomeric article is a vehicle tire or a component thereof.

15. The vulcanized elastomeric article of claim 14 wherein said component is a sidewall.

16. The vulcanized elastomeric article of claim 14, wherein said component is a tread.

17. A combustible fuel composition comprising a combustible fuel and the compound of claim 1.

18. A fuel additive composition comprising a fuel additive and the compound of claim 1.

19. A method of making the compound of claim 1, comprising:
reacting a compound of formula II

II wherein $R_1$ is selected from the group consisting of a hydrogen atom and an alkyl group having from 1 to 2 carbon atoms;

wherein $R_2$ is selected from the group consisting of an alkylene group having from 1 to 12 carbon atoms, an arylene group having from 5 to 18 carbon atoms, and a heterocyclic group having from 5 to 12 carbon atoms;

wherein M is selected from the group consisting of a monovalent metallic cation, a multivalent metallic cation, and an ammonium or alkyl ammonium cation, with a dithiocarbamate salt corresponding to formula III

III wherein R and R' are independently selected from the group consisting of a hydrogen atom, an alkyl group, an aryl group, and an alkylaryl group; and M' is selected from the group consisting of a monovalent metallic cation, a multivalent metallic cation, and an ammonium or alkyl ammonium cation.

20. The method of claim 19, wherein the compound of formula II is sodium S,S',S"-((1,3,5-triazinane-1,3,5-triyl)tris(propane-3,1-diyl))tris(sulfuro-thioate), and the compound of formula III is sodium dibenzyldithiocarbamate.

* * * * *